US009303292B2

(12) United States Patent
Shawky Abduo et al.

(10) Patent No.: US 9,303,292 B2
(45) Date of Patent: Apr. 5, 2016

(54) DIRECT DETECTION OF UNAMPLIFIED HEPATITIS C VIRUS RNA USING UNMODIFIED GOLD NANOPARTICLES

(75) Inventors: Sherif Mohamed Shawky Abduo, Cairo (EG); Hassan Mohamed El-Said Azzay El-Badawy, Alexandria (EG)

(73) Assignee: The American University of Cairo, New Cairo (EG)

( * ) Notice: Subject to any disclaimer, the term of this patent is extended or adjusted under 35 U.S.C. 154(b) by 878 days.

(21) Appl. No.: 12/987,659

(22) Filed: Jan. 10, 2011

(65) Prior Publication Data
US 2013/0236880 A1    Sep. 12, 2013

(51) Int. Cl.
*C12Q 1/70* (2006.01)
*B82Y 15/00* (2011.01)

(52) U.S. Cl.
CPC *C12Q 1/707* (2013.01); *C12Q 1/70* (2013.01); *B82Y 15/00* (2013.01); *Y10S 977/81* (2013.01); *Y10S 977/924* (2013.01)

(58) Field of Classification Search
CPC .................................................. C12Q 1/6818
See application file for complete search history.

(56) References Cited

U.S. PATENT DOCUMENTS

| 6,083,482 A | 7/2000 | Wang |
| 7,473,773 B2 | 1/2009 | Elagin et al. |
| 8,071,750 B2 | 12/2011 | Elagin et al. |
| 2004/0229253 A1* | 11/2004 | Hyldig-Nielsen et al. ........ 435/6 |
| 2008/0311669 A1 | 12/2008 | Mirkin et al. |
| 2009/0111092 A1 | 4/2009 | Elagin et al. |
| 2009/0123916 A1 | 5/2009 | La Scola et al. |
| 2011/0008772 A1 | 1/2011 | Lai et al. |

FOREIGN PATENT DOCUMENTS

| EP | 1002878 A2 * | 11/1999 | ............... C12Q 1/70 |
| WO | WO2009/131661 A2 * | 10/2009 | .............. C12P 21/06 |

OTHER PUBLICATIONS

Shawky et al. (Clinical Biochemistry, Aug. 2010, vol. 43, p. 1163-1168).*
Baptista et al. (Analytical Bioanalytical Chemistry, 2008, vol. 391, p. 943-950).*
Glynou et al. (Analytical Chemistry, 2003, vol. 75, 4155-4160).*
Nakano et al. (JID, 2004, vol. 190, p. 1098-1108).*
Office Action issued Aug. 14, 2014 in European Patent Application No. 11855330.4.
Higuchi et al, Epidemiology and Clinical Aspects on Hepatitis C. Jpn J Infect Dis 55 (2002) 69-77.
Lauer et al, Hepatitis C Virus Infection. N Engl J Med 345 (2001) 41-52.
Strader et al, Diagnosis, Management, and Treatment of Hepatitis C. Hepatology 39 (2004) 1147-71.
Marcellin, Hepatitis C: clinical spectrum of the disease. J Hepatol. 31 (1999) 9-16.
Sarrazin, Diagnosis of hepatitis C: update 2004. J Gastroenterol Hepatol J Gastroenterol Hepatol (2004) S88-S93.
Scott et al, Molecular Diagnostics of Hepatitis C Virus Infection: A Systematic Review. JAMA 297 (2007) 724-732.
Jain, Nanotechnology in clinical laboratory diagnostics. Clin Chim Acta 358 (2005) 37-54.
Jain et al, Calculated Absorption and Scattering Properties of Gold Nanoparticles of Different Size, Shape, and Composition: Applications in Biological Imaging and Biomedicine. J. Phys. Chem. B 110 (2006) 7238-7248.
Li et al, Label-Free Colorimetric Detection of Specific Sequences in Genomic DNA Amplified by the Polymerase Chain Reaction. J. Am. Chem. Soc. 126 (2004) 10958-10961.
Huang et al, Gold nanoparticles: interesting optical properties and recent applications in cancer diagnostics and therapy. Nanomed 2 (2007) 681-91.
Radwan et al, Gold nanoparticles for molecular diagnostics. Expert Rev Mol Diagn 9 (2009) 511-24.
Li et al, Colorimetric detection of DNA sequences based on electrostatic interactions with unmodified gold nanoparticles. Proc Natl Acad Sci U S A 101 (2004) 14036-39.
Griffin, et al, Size- and distance-dependent nanoparticle surface-energy transfer (NSET) method for selective sensing of hepatitis C virus RNA. Chemistry 15 (2009) 342-51.
Griffin et al, Sequence-specific HCV RNA quantification using the size-dependent nonlinear optical properties of gold nanoparticles. Small 5 (2009) 839-45.
Storhoff et al, One-Pot Colorimetric Differentiation of Polynucleotides with Single Base Imperfections Using Gold Nanoparticle Probes. J. Am. Chem. Soc. 120 (1998) 1959-1964.
Liu et al, Extinction coefficient of gold nanoparticles with different sizes and different capping ligands. Colloids Surf B Biointerfaces 58 (2007) 3-7.
Otto et al, Separate Isolation of Genomic DNA and Total RNA from Single Samples Using the SV Total RNA, promega notes, No. 69 (1998) 19-24.
Sisco, Is RNA in serum bound to nucleoprotein complexes? Clin Chem 47 (2001) 1744-5.
Seme et al, The role of core antigen detection in management of hepatitis C: a critical review. J Clin Virol 32 (2005) 92-101.

(Continued)

*Primary Examiner* — Agnieszka Boesen
(74) *Attorney, Agent, or Firm* — Oblon, McClelland, Maier & Neustadt, L.L.P

(57) ABSTRACT

A gold nanoparticle-based colorimetric assay kit for hepatitis C virus RNA that detects unamplified HCV RNA in clinical specimens using unmodified AuNPs and oligotargeter polynucleotides that bind to HCV RNA. A method for detecting hepatitis C virus comprising contacting a sample suspected of containing hepatitis C virus with a polynucleotide that binds to hepatitis C virus RNA and with gold nanoparticles, detecting the aggregation of nanoparticles, and detecting hepatitis C virus in the sample when the nanoparticles aggregate (solution color becomes blue) in comparison with a control or a negative sample not containing the virus when nanoparticles do not aggregate (solution color remains red).

28 Claims, 6 Drawing Sheets
(5 of 6 Drawing Sheet(s) Filed in Color)

(56) References Cited

OTHER PUBLICATIONS

El Awady et al, Positional effect of mutations in 5'UTR of hepatitis C virus 4a on patients' response to therapy. World J Gastroenterol 15 (2009) 1480-6.

Wang et al, A label-free biosensor based on gold nanoshell monolayers for monitoring biomolecular interactions in diluted whole blood. Biosens Bioelectron 23 (2008) 1166-70.

Dykman, Gold nanoparticles: preparation, functionalisation and applications in biochemistry and immunochemistry. Russian chemical Reviews 76 (2007) 181-194.

Green et al, A simple one phase preparation of organically capped gold nanocrystals. Chemical Communications (2000) 183-184.

Parab et al.—A gold nanorod-based optical DNA biosensor for the diagnosis of pathogens, 2010, Biosensors and Bioelectronics, 26, pp. 667-673.

Qin et al.—Size control over spherical silver nanoparticles by ascorbic acid reduction, 2010, Colloids and Surfaces A: Physicochem. Eng. Aspects, 372, pp. 172-176.

Ma et al.—Optical DNA detection based on gold nanorods aggregation, 2010, Analytica Chimica Acta, 673, pp. 179-184.

Fricke, W. Florian, et al., "Comparative Genomics of the IncA/C Multidrug Resistance Plasmid Family", Journal of Bacteriology, vol. 191, No. 15, pp. 4750-4757, Aug. 2009.

Kim, Eun-Young et al., "A real-time PCR-based method for determining the surface coverage of thiol-capped oligonucleotides bound onto gold nanoparticles", Nucleic Acids Research, vol. 34, No. 7, pp. e54 1-7, Apr. 2006.

Ullrich, P. et al, "Detection, Semiquantitation, and Genetic Variation in Hepatitis C Virus Sequences Amplified from the Plasma of Blood Donors with Elevated Alanine Aminotransferase", Journal of Clin. Invest. vol. 86, No. 5, pp. 1609-1614, Nov. 1990.

International Search Report Issued Sep. 7, 2012 in PCT/US12/32778.

International Search Report issued Oct. 1, 2013 in PCT/US2013/024136.

Rui Cao et al., "Naked Eye Sensitive Detection of Nuclease Activity Using Positively-charged Gold Nanoparticles as Colorimetric Probes", Chemical Communications, vol. 47, 2011, pp. 12301-12303.

Ramsey C. Cheung et al., "Rapid and Sensitive Method for Detection of Hepatitis C Virus RNA by Using Silica Particles", Journal or Clinical Microbiology, vol. 32. No. 10, 1994, pp. 2593-2597 and Cover page.

Lijun Hong et al., "Synthesis of Flower-like Silver Nanoarchitectures at Room Temperature", Materials Research Bulletin, vol. 44, Issue 6, 2009, pp. 1201-1204.

Jung-Won Kim et al., "An Operationally Simple Colorimetric Assay of Hyaluronidase Activity Using Cationic Gold Nanoparticles", Analyst, vol. 134, 2009, pp. 1291-1293 and Supplementary Information pp. (1-3).

NCBI, GenBank accession No. NC009824.1 (Jul. 27, 2011).

Communication pursuant to Rules 70(2) and 70a(2) EPC issued Mar. 27, 2015 in European Search Report No. 12768288.8.

Partial European Search Report issued Nov. 11, 2014 in Patent Application No. 12768288.8.

Hosub Lee, et al., "Colorimetric genotyping of single nucleotide polymorphism based on selective aggregation of unmodified gold nanoparticles" Biosensors and Bioelectronics, vol. 26, No. 2, XP027320379, Oct. 2010, pp. 730-735.

Fan Xia, et al., "Colorimetric detection of DNA, small molecules, proteins, and ions using unmodified gold nanoparticles and conjugated polyelectrolytes" Center for Polymers and Organic Solids, Proceedings of the National Academy of Sciences, vol. 107, No. 24, XP055141430, Jun. 2010, pp. 10837-10841.

Ye Lim Jung, et al., "Direct colorimetric diagnosis of pathogen infections by utilizing thiol-labeled PCR primers and unmodified gold nanoparticles" Biosensors and Bioelectronics, vol. 25, No. 8, XP026941415, Apr. 2010, pp. 1941-1946.

Marion Stoffels, et al., "rRNA probe-based cell fishing of bacteria" Environmental Microbiology, vol. 1, No. 3, XP002246085, Jun. 1999, pp. 259-271.

Michael Wagner, et al., "Development of an rRNA-Targeted Oligonucleotide Probe Specific for the Genus *Acinetobacter* and Its Application for In Situ Monitoring in Activated Sludge" Applied and Environmental Microbiology, American Society for Microbiology, vol. 60, No. 3, XP002097846, Mar. 1994, pp. 792-800.

Office Action dated Jan. 21, 2016 issued in corresponding EP patent application No. 11 855 330.4.

Egyptian Office Action dated Dec. 22, 2015 issued in corresponding EG patent application No. 2013071158.

\* cited by examiner

DIRECT DETECTION OF UNAMPLIFIED HEPATITIS C VIRUS RNA USING UNMODIFIED GOLD NANOPARTICLES

CROSS-REFERENCE TO RELATED APPLICATIONS (None)

STATEMENT REGARDING FEDERALLY SPONSORED RESEARCH OR DEVELOPMENT (None)

REFERENCE TO MATERIAL ON COMPACT DISK (None)

BACKGROUND OF THE INVENTION

1. Field of the Invention

A gold nanoparticle-based colorimetric assay for hepatitis C virus RNA that detects unamplified HCV RNA in clinical specimens using unmodified gold nanoparticles ("AuNPs").

2. Description of the Related Art

Gold nanoparticles or AuNPs exhibit a unique phenomenon known as Surface Plasmon Resonance, which is responsible for their intense red color in suspension. This color changes to blue upon aggregation of AuNPs.

According to the World Health Organization, there are around 200 million people worldwide infected with hepatitis C virus ("HCV"), with three to four million newly infected patients annually [1]. HCV is a small enveloped single-stranded RNA virus that belongs to the *Flaviridae* family, *Hepacivirus* genus, which comprises a group of highly variable strains or isolates. HCV is a blood borne virus and infection has different clinical outcomes ranging from acute resolving hepatitis to chronic liver diseases, including liver fibrosis, cirrhosis and hepatocellular carcinoma [2; 3; 4]. The acute viral infection resolves in 15% of infected patients but progresses in 85% of patients to chronic infection [5].

Different HCV isolates frequently exhibit genetic differences and HCV isolates have been classified into six different genotypes, which are further grouped into subtypes identified by letter designations, e.g. HCV Genotype 1a. Different HCV genotypes predominate in particular parts of the world. For example, in North America genotype 1a predominates, followed by genotypes 2a, 2b, 2c, and 3a. Genotypes 4 and 5 are found almost exclusively in Africa. The genotype of HCV is clinically significant in determining therapeutic response, such as responses to interferon-based therapy. Prior infection with one HCV genotype does not necessarily confer protection against another. Genotypes have up to 67% percent nucleotide similarity to one another and subtypes have nucleotide similarity up to 78%. More than 80 different subtypes have been identified. HCV isolates that have sequence similarity between 91-99% are termed quasispecies.

Currently HCV is detected using immunoassays, such as antibody-based immunoassays and confirmed by molecular assays, such as RT-PCR. For example, immunoassays such as enzyme linked immunoassays (EIAs) and recombinant immune blot assays (RIBA) are used for detection of anti-HCV antibodies [6] and conventional RT-PCR and transcription-mediated amplification (TMA) are used for qualitative detection of HCV RNA while quantitative detection is achieved using real-time RT-PCR, and/or branched DNA-based assays [7].

Despite the high sensitivity and specificity of these methods, they are time-consuming, labor intensive, expensive, and require specialized equipment and thus are not suitable for use in many developing countries or for use in the field. Therefore, there is a great need to develop a low-tech assay for the direct detection of unamplified HCV RNA with acceptable sensitivity and specificity, short turnaround time, and cost-effectiveness. Such an assay would be critical to characterize and control HCV in developing countries with limited resources and high infection rates, such as Egypt.

Nanoparticles have been recently proposed as promising tools to develop the next generation of diagnostic assays. Because of their unique properties and ability to interact with biomolecules on one-to-one basis, various nanoparticles show great promise to meet the rigorous demands of the clinical laboratory for sensitivity and cost-effectiveness, and can be used in the future in point-of-care diagnosis [8].

Gold nanoparticles ("AuNPs") are spheres with a typical diameter of approximately 2-50 nm. They exhibit a unique phenomenon known as Surface Plasmon Resonance (SPR), which is responsible for their intense red color, and which changes to blue upon aggregation of AuNPs [9].

The addition of salt shields the surface charge on the AuNPs, which are typically negatively charged owing to adsorbed negatively charged citrate ions on their surfaces, leading to aggregation of AuNPs and a red-to-blue color shift [10]. SPR is also responsible for the large absorption and scattering cross-sections of AuNPs which are 4-5 orders of magnitude larger than those of conventional dyes [11]. These unique optical properties have allowed the use of AuNPs in simple and rapid colorimetric assays for clinical diagnosis offering higher sensitivity and specificity than current detection techniques [12, 13]. Suitable components and procedures for making gold nanoparticles are known in the art and are incorporated by reference to the articles cited herein.

Li et al. developed a colorimetric assay using unmodified citrate-coated AuNPs [10, 13]. This method is based on the property of single-stranded DNA (ssDNA) which adsorbs on citrate-coated AuNPs. This adsorption increases the negative charge on the AuNPs leading to increased repulsion between the particles, thus preventing aggregation. The adsorption of ssDNA on AuNPs occurs due to the fact that ssDNA can uncoil and expose its nitrogenous bases. The attractive electrostatic forces between the bases and the AuNPs allow adsorption of the ssDNA. On the other hand, double-stranded DNA (dsDNA) does not adsorb on AuNPs due to the repulsion between its negatively-charged phosphate backbone and the negatively-charged coating of citrate ions on the surfaces of the AuNPs. Therefore, when AuNPs are added to a saline solution containing the target DNA and its complementary unlabeled single-stranded polynucleotide, AuNPs aggregate (since the single-stranded polynucleotides are not free to stabilize the AuNPs) and the solution color changes to blue. However, in the absence of the target or the presence of a non-complementary target, the complementary single-stranded polynucleotides are free to stabilize the AuNPs thus preventing their aggregation and the solution color remains red. This method has been used to detect single nucleotide polymorphisms in PCR-amplified genomic DNA extracted from clinical samples [10]. Moreover, based on the same principle, AuNPs are capable of quenching fluorescent dyes and this property has been used for detection of synthetic HCV sequences with high sensitivity and selectivity [14, 15]. Shawky, et al., Clin. Biochem. 43:1163-1168 (2010), which is incorporated by reference, discloses direct detection of unamplified hepatitis C virus RNA using unmodified gold nanoparticles.

BRIEF SUMMARY OF THE INVENTION

In distinction to the background art, the inventors have discovered that an AuNPs-based colorimetric method can be used to directly detect unamplified HCV RNA extracted from clinical specimens as depicted by FIG. 1 and have produced a simple, rapid, and sensitive colorimetric assay that can sensitively detect HCV in clinical samples even under field conditions.

HCV RNA is extracted or purified from a clinical sample without amplification and is hybridized to an unlabeled complementary polynucleotide sequence ("oligotargeter"). Salt, oligotargeter, AuNP concentrations, denaturation and annealing temperatures and time are carefully selected to maximize assay sensitivity and specificity as described below. This hybridization takes place before the addition of gold nanoparticles (AuNPs) under conditions which do not affect the stability of the colloidal gold nanoparticles. Surprisingly, this procedure provides a high sensitive, rapid, simple and cheap way to directly detect unamplified HCV RNA in clinical samples and does not require polynucleotide labeling or modification of gold nanoparticles. In one embodiment, this assay is demonstrated to have a sensitivity of 92% and a specificity of 88.9% in detecting HCV in clinical samples and is capable of detecting 20 copies of HCV/reaction colorimetrically, i.e., by a color change from red to blue. The developed assay is highly sensitive, has excellent specificity for HCV and can be performed very quickly, e.g., has a turnaround time of 30 min. It also eliminates the need for thermal cycling and detection instruments. It is believed that this is the first assay that allows the detection of unamplified HCV RNA in clinical specimens using unmodified AuNPs.

One aspect of the invention is a method for detecting hepatitis C virus comprising contacting a sample suspected of containing hepatitis C virus with an oligotargeter polynucleotide that binds to hepatitis C virus RNA and with gold nanoparticles, detecting the aggregation of nanoparticles, and detecting hepatitis C virus in the sample when the nanoparticles aggregate (indicated by a colorimetric change to blue). Colorimetric change may also be determined by comparison to a control sample not containing the virus (solution color remains red). The HCV assay of the invention is generally performed after exposure of RNA from a clinical sample to conditions which would denature or unfold hepatitis C RNA.

The sample may optionally be extracted, isolated or purified by a conventional method or by use of a commercial kit for this purpose and may be stored, diluted or serially diluted prior to assay. The sample may be a clinical sample from a normal subject or generally from a subject suspected of having been exposed to or diagnosed as having HCV. Clinical samples include blood, plasma or serum, which may contain preservatives such as EDTA. Other biological samples such as spinal fluid, semen, mucosal secretions, saliva, sweat, urine, etc. may be used. Samples may be obtained from subjects having acute, chronic or occult HCV infection. Two or more samples may be obtained longitudinally from a subject undergoing treatment for HCV treatment. Samples may also be obtained from a subject after cessation of anti-HCV therapy, for example, at least 24 weeks after cessation of anti-HCV therapy.

In general, the gold nanoparticles will have an average diameter ranging from 12 to 20 nm and be spherical, they may also range from 15-18 nm in diameter.

The oligotargeter single-stranded polynucleotide that binds to hepatitis C RNA preferably comprises a portion of a 5' untranslated region of hepatitis C genomic RNA, but it may also be selected from portion of hepatitis C genomic RNA other than the 5' untranslated region. Generally, the oligotargeter will contain 20 to 30 contiguous nucleotides of the HCV genome, or any intermediate value between 20 and 30. It may consist of or comprise any one of the sequences shown by SEQ ID NOS: 3-11 or SEQ ID NO: 12 oligotargeter 5'TAC-CACAAGGCCTTTCGCGACCCAACA'3 (SEQ ID NO: 12). The oligotargeter sequence may be specific to one particular HCV genotype, subtype or quasispecies or may bind to two or more or all HCV genotypes, subtypes or quasispecies, or to a particular subspecies or quasispecies of HCV.

The presence of HCV in a sample may be detected by a colorimetric change of a sample after contacting it with gold nanoparticles. Nonaggregated gold nanoparticles exhibit a red color and aggregated gold nanoparticles a blue color, where a blue color is indicative of the presence of HCV RNA in a sample that is complementary to the oligotargeter is conjugated to an FAM dye or other fluorescent dye or fluorophore whose emission can be quenched by gold nanoparticles; and the presence of HCV is detected by the emission of fluorescence.

The assay may also further comprise determining an HCV genotype and subtype of HCV in the sample by detecting SNPs in PCR-amplified or unamplified sequences from HCV core, 5'UTR, or NS5B regions.

Another aspect of the invention is a kit comprising gold nanoparticles, an oligotargeter that binds to hepatitis C virus RNA, and optionally, an RNA extraction kit, at least one of the following ingredients a biological sample preservative or additive, an RNA extractant buffer, a reaction buffer, a negative control sample, a positive control sample, a reaction container, a colorimetric chart, a packaging material, an instruction for use in detecting hepatitis C virus.

BRIEF DESCRIPTION OF THE DRAWINGS

The patent or application file contains at least one drawing executed in color. Copies of any resulting patent or patent application publication with color drawing(s) will be provided by the office upon request and payment of the necessary fee.

DETAILED DESCRIPTION OF THE INVENTION

Figure 1:
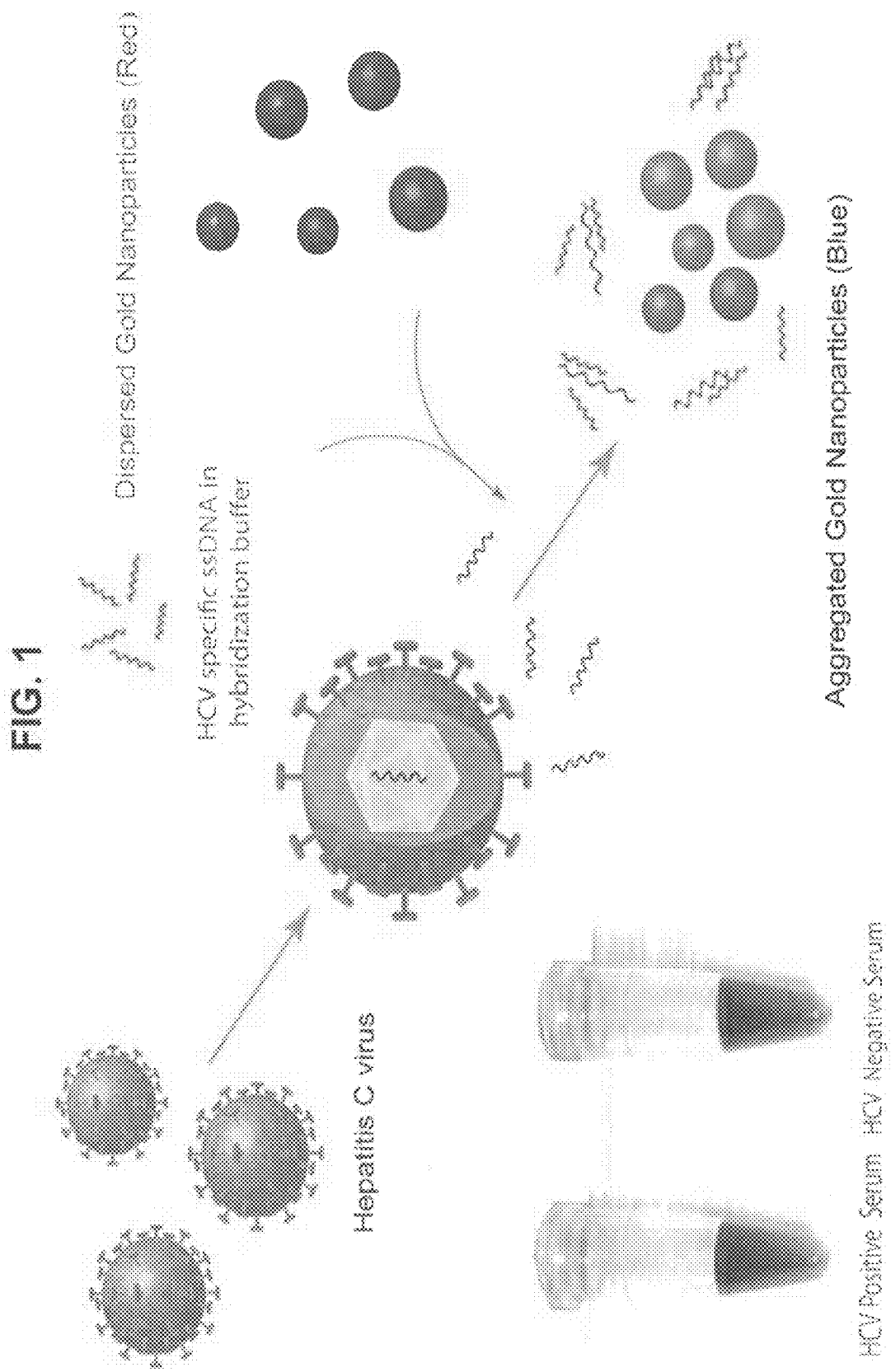
FIG. 1. Schematic diagram of a colorimetric assay based on unmodified AuNPs for detection of full length HCV RNA. First, the tertiary structure of the target RNA in hepatitis C virus (appearing in the upper left and center of FIG. 1) is denatured and the complementary oligotargeter (upper center, "HCV specifics ssDNA" hybridizes to the target forming double strands (lower right). Upon adding AuNPs (upper right) they will aggregate since there are no free oligotargeter to stabilize the AuNPs, and the solution color changes from red to blue (lower right, "Aggregate Gold Nanoparticles"). In the presence of a non-complementary target RNA, the oligotargeter will be free to bind and stabilize the AuNPs thus preventing their aggregation and the solution color remains red (upper right, "Dispersed Gold Nanoparticles").

A colorimetric assay has been developed using unmodified AuNPs for the direct detection of unamplified HCV RNA in biological fluids without the need for RNA amplification. The assay has a detection limit of 20 copies/reaction which is significantly better than that of the commercially available HCV core antigen test that detects HCV in samples with viral load above 20,000 IU/mL (one IU is typically equivalent to 3-5 copies) [20]. The highly sensitive assay of the invention can be applied for tracking HCV replication even at low viral titers.

The invention has several other advantages in addition to its high sensitivity including excellent specificity, short turn-around time, and cost effectiveness. The assay is economical, for example, 1 gram of gold is sufficient to prepare 1 liter of 15 nm gold nanoparticles and only about 10 μL of gold nanoparticles are required per assay. Thus, based on a cost of 1 gram of gold chloride of about 200 euros, the assay is highly cost effective. While the cost of RNA extract kits used to extract HCV RNA from clinical samples may vary, this cost generally ranges between 100-200 euros for 50 extractions and thus the overall cost of this assay is low, especially compared to more complicated prior art assays. Moreover, the use of AuNPs eliminates the need for expensive detection instrumentation and does not require functionalization of the AuNPs, the oligotargeter, or the target. Since HCV RNA extraction is easy and takes less than 20 min using commercial kits that are based on silica column extraction, magnetic beads, or organic extraction, the overall time required for extracting a clinical sample and obtaining the assay result is very short. Furthermore, the detection limit of the assay can be increased simply by increasing the starting serum volume used for RNA extraction.

Moreover, this assay may be adapted into a quantitative test by spectrophotometric quantification of the resulting blue color against a standard curve or developing a fluorometric version of the test by utilization of the size and distance nanoparticle surface energy transfer (NSET) properties of AuNPs.

The assay of the invention may be further modified to detect SNPs in HCV sequences, for example to discriminate between genotypes or even quasispecies by manipulating the annealing temperature of the oligotargeters. This has great implications for HCV genotyping, subtyping, and monitoring of viral factors that have been correlated to patient's response to interferon therapy [21].

Consequently, the invention permits use of unmodified AuNPs for direct detection of unamplified HCV RNA in clinical specimens and may be competitively used in place of other commercial immunoassays and RT-PCR methods as routine tests for management of HCV patients.

The following abbreviations and terms appear herein.
ALT: alanine aminotransferase.
AST: aspartate aminotransferase.
HCV: Hepatitis C virus.
EIA: Enzyme Linked Immuno-assays.
RIBA: Recombinant immune blot assays.
RT-PCR: Reverse Transcriptase-Polymerase Chain Reaction.
SNPs: Single Nucleotide Polymorphisms.
AuNPs: Gold Nanoparticles.
SPR: Surface Plasmon Resonance.

The term "sample" describes any type of sample suspected to contain HCV or to be assayed for detection of HCV. Generally, a biological sample from a subject suspected of being exposed to or having HCV infection will be used, such as blood, plasma or serum, or other bodily fluids that may contain HCV. These may include, for example, plasma, serum, spinal fluid, lymph fluid, secretions from the respiratory, gastrointestinal, or genitourinary systems including tears, saliva, milk, urine, semen, hepatocytes, and red or white blood cells or platelets. Samples may also be obtained from tissue cell culture, such as cultured hepatocytes or leukocytes, and constitute cells, including recombinant cells, or medium in which HCV may be detected. In some cases a tissue sample may be used in the assay or processed for use in the assay, for example, by a conventional method used to extract HCV or HCV nucleic acids from the sample.

The term "purified HCV" describes HCV which has been isolated from the host tissues or fluids in which the virus is normally associated, isolated from a tissue cell culture, or separated from other types of microorganisms, such as bacteria or other viruses. Techniques for isolating HCV are known to those of skill in the art.

The term "preservative or additive for a sample" includes additives such as heparin or EDTA. The term also includes other agents which prevent degradation of HCV RNA or permit HCV RNA to be easily recognized in the method of the invention. These include normal saline or commercially available preservatives such as the one found in PAX gene tubes. The term "extraction buffer" refers to conventional agents and materials useful for extracting, purifying or isolating HCV RNA from a sample, such as a biological sample like serum.

The term "denaturation" refers to a process of unfolding HCV RNA. For example, by heating a sample to 65, 75, 85, 90, 95-100° C. Denaturation may also be facilitated by addition of other ingredients such as salts, formamide, or sodium hydroxide.

The term "reaction buffer" describes a composition in which the sample, gold nanoparticles and polynucleotide that binds to HCV RNA interact. Exemplary buffers include phosphate buffer saline, and other buffers used in the PCR reaction mixtures. As used herein, the term "oligotargeter" describes a "polynucleotide that binds to hepatitis C virus RNA" and refers to a polynucleotide which can form a hybrid structure with a sequence in a target region of the HCV genomic RNA through complementarity with a sequence in the HCV genomic RNA. The oligotargeter will be long enough to bind to HCV RNA (or for some applications HCV cDNA) in a sample. Preferably, it will comprise 19, 20, 21, 22, 23, 24, 25, 26, 27, 28, 29, 30 or 31 bp. If the sequence is less than 19 bp, then performance will be reduced because shorter sequence will bind to non-specific sequences which would result in false positive results or if it exceeds 31 bp, then performance will be reduced because of dimerization and hairpin formation of longer polynucleotides leading also to false positive results.

The oligotargeter may correspond to any portion of the HCV genomic DNA, but preferably will be selected to bind to the 5' untranslated region because this region is highly conserved and can be used to differentiate between different HCV genotypes.

For detection of HCV infection, preferably the oligotargeter will bind to an HCV genomic sequence shared by all genotypes of HCV. An example of such an HCV-specific sequence (SEQ ID NO: 12) is shown below. This is a highly-specific polynucleotide sequence for detection of HCV and was designed to target a conserved region in the 5'UTR OF HCV RNA. This region is highly conserved in all HCV genotypes and subtypes. Moreover, this sequence has not been reported before in literature and is not complementary to any of the human mRNA which increases the test specificity. Other HCV-specific oligotargeter sequences comprising the preferred sequence below or constituting fragments of this sequence having a length ranging from 19 to 31 bp may also be designed, including modifications as described below, though a preferred polynucleotide sequence is:

5' TACCACAAGGCCTTTCGCGACCCAACA'3. (SEQ ID NO: 12)

For applications in which it is desired to detect different genotypes or subtypes of HCV, the polynucleotide sequence will be selected to bind to a sequence unique to the particular genotype(s) or subtype(s) of HCV to be detected. Hepatitis C Virus (HCV) is classified into six genotypes with more than 80 subtypes. These genotype-specific sequences may be selected and identified by the following method. An oligotargeter complementary to the sequence of an HCV genotype is designed for each genotype to be used in the HCV detection assay described herein. Genotyping is mainly done for HCV by selecting an oligotargeter sequence complementary to the 5'UTR, core and/or NS5b regions of the virus. The procedures used to identify and select the genotype-specific oligotargeters shown in the table below are as follows. All the HCV sequences on the HCV database (http://_hcv.lanl.gov/content/index) for a specified genotype and a specified region on HCV genome (core and/or NS5b nucleotides sequences) were retrieved. Comparisons of the sequences were performed using the freeware SeaView, version 4.0 and the sequences which are specific for the specific genotype were selected and aligned in the HCV database will all the genotypes and subtypes of HCV. However, other databases of HCV sequences and other available comparison algorithms or software may be employed as well to identify genotype specific sequences. The selected putative oligotargeter sequences were further modified using the BLAST program by sequence alignment of a selected sequence in the HCV database. The following nine HCV-specific genotype-specific oligotargeter sequences were identified after careful selection for their HCV genotypic specificity by the inventors.

Other genotype-specific oligotargeter sequences comprising these sequences or fragments of these sequences having a length ranging from 19 to 31 bp may also be designed, though the preferred sequences as shown in the table above.

The term "modified oligotargeter" describes an oligotargeter sequence that may contain one or more modified bases or contain a modification to or replacement of the phosphate backbone structure of a conventional oligonucleotide but otherwise substantially maintain its ability to hybridize to a target sequence, such as HCV RNA. For example, a modification to oligotargeter sequence that increases stability or resistance to degradation or improves binding specificity or sensitivity may be made. Examples of modifications to increase nuclease resistance of the oligotargeter include the following: (a) phosphothioate modified sequence (where one of the oxygen on the phosphate of phosphodiester bond is replaced with a sulphur atom); (b) 3'-propryl group (C3 spacer, adding a propyl group at the 3' end); and (c) Inverted end (3'-3' linkage), though other modifications known to those in the art may also be employed.

For some applications they may contain one, two, three, four or more degenerate bases, which can base pair with A, T, G, C and/or U. Degenerate bases may be incorporated into an oligotargeter to increase its affinity for the HCV target sequence. For example, an oligotargeter containing one, two, three, four or more degenerate bases (e.g. inosine) in its oligonucleotide sequence can be used to overcome or compensate for a mutation that may occur within the same genotype and subtype (quasispecies). Inosine resembles guanine, but without the 2-amino group, and can form stable (wobble) base pairs with adenine, cytosine and uracil that are similar in terms of interaction strength. Therefore, inosine in a probe can bind to perfectly complementary polynucleotide or ones that have mismatches at the location of the inosine to form duplex structures of comparable stability.

An oligotargeter may also be modified by conjugation to a detectable moiety, such as a fluorophore. For example, the 5' end of a oligotargeter polynucleotide sequence may be conjugated to an FAM dye whose fluorescence can be quenched by gold nanoparticles.

The term "target region" describes the portion of the HCV genomic RNA to which the polynucleotide binds. For example, the target region may lie in the 5' untranslated region of the HCV genomic RNA. However, regions from which polynucleotide sequences include, but are not limited to

| Genotype | Sequence | Length (nucleotides) | Position related to H77 isolate | SEQ ID NO: |
|---|---|---|---|---|
| 1a | CACAGATAACGACTAAGTCGTCGCCACACAC | 31 | 8544-8574 | 3 |
| 1b | GCCTTGGGGATAGGTTGTCGCCTTCCA | 27 | 518-544 | 4 |
| 2a | TAGGGGCCAGGGGTATCCTGGTTTT | 25 | 572-596 | 5 |
| 2b | CAGAGGCCAAGGATATCCTGGCTTT | 25 | 572-596 | 6 |
| 3 | CGCCTTGGGGATAGGCTGTCG | 21 | 525-545 | 7 |
| 4 | TCCTGGTTGTGCCCAGGACCTTCCCT | 26 | 556-581 | 8 |
| 5 | TTGCGACCGTTCCGAATTCTTCCGA | 25 | 488-512 | 9 |
| 6a | CCTTTAGTACATCCTGATAATGT | 23 | 7787-7809 | 10 |
| 6b-n | CAGCCCTCATTCCCATAAAG | 20 | 594-613 | 11 | regions encoding specific epitopes, as well as control or promoter segments and non-transcribed and/or non-translated regions.

The term "HCV RNA" refers to RNA from a HCV viral genome or synthetic RNA corresponding to genomic sequences, fragments thereof, transcripts thereof, or modified or mutant sequences derived HCV sequences. It also encompass modified or mutated HCV genomic sequences, such as variants containing one or more single nucleotide polymorphisms, or more generally, those having a sequence containing 1, 2, 3, 4, 5 or more insertions, deletions, transpositions, or substitutions to a genomic HCV sequence.

The term "HCV cDNA" describes DNA complementary to HCV RNA.

"Hybridization buffer" refers to any buffer that permits hybridization to occur between an oligotargeter sequence and HCV RNA, for example, 10 mM phosphate buffered saline (PBS), pH 7.0. Samples are admixed with the oligotargeter in hybridization buffer and subsequently denatured and annealed prior to admixture with gold nanoparticles. A preferred buffer is phosphate-buffered saline ("PBS"), pH 7.0-7.4. Monovalent cation (e.g., sodium or potassium) salt concentration can range from 50 mM to 300 mM. Suitable hybridization buffers and protocols are well-known in the art and are incorporated by reference to Maniatis, et al., *Molecular Cloning: A Laboratory Manual*, 2$^{nd}$ edition or *Current Protocols in Molecular Biology*, vol. 1 (updated October, 2010). However, salt concentration is dependent on the gold nanoparticles volume and concentration.

The term "citrate buffer" describes a buffer containing citrate used to prepare or suspend the colloidal gold nanoparticles (AuNPs). Alternatively, a buffer containing hydrazine, L-tryptophan, an alcohol, especially a lower $C_1$-$C_6$ alcohol, an ether, or sodium diphenyl aminosulfonate may be used. A preferred salt is trisodium citrate salt at a concentration of 30-50 mM or 1-2 wt % (no specific pH). Suitable buffers and methods for making and using colloidal gold are incorporated by reference to John Turkevich. Colloidal gold. Part I. Gold Bull. 1985; 18(3): 86-92; John Turkevich. Colloidal gold. Part II. Gold Bull. 1985; 18(4):125-131; and Katherine C. Graber, R. Grissith Freeman, Micheal B. Hommer, Micheal J. Natan. Preparation and characterization of gold colloid monolayers. Analytical Chemistry 1995; 67(4): 735-743.

The term "gold nanoparticle" refers to spherical gold nanoparticles. Generally, the gold nanoparticles are produced by citrate reduction method and have an average diameter ranging from 2.0 nm to 100 nm, preferably, an average diameter ranging from 10 to 25 nm, and more preferably from 15 to 20 nm. When the size of the gold nanoparticle is too small, then performance is reduced because surface-plasmon resonance would be reduced and completely abolished for particles <2 nm and the color change will not be observed and when it is too large, then performance is reduced because the aggregation affinity of the nanoparticles would be higher leading to false positive results.

The gold nanoparticles used in the invention may be produced or synthesized by methods known in the art, such as those described above in the background section. Alternatively, exemplary methods include (a) by reduction of chloroauric acid with sodium borohydride [22]; (b) By reduction of chloroauric acid with hydrogen peroxide [23]; or (c) by a single phase microemulsion method [24]. These methods of producing gold nanoparticles are hereby incorporated by reference to the articles cited above.

"Fluorometric detection" of HCV refers to a method in which a fluorescent dye, such as a fluorescein derivative like FAM (Fluorescein amidite) dye or other fluorophore, has been conjugated to the 5'end of the oligotargeter sequence as described above and used to develop a nanoparticle surface energy transfer (NSET)-based detection assay. For example, an FAM molecule is quenched in the absence of HCV RNA by the gold nanoparticles, while in the presence of HCV RNA, hybridization occurs between the oligotargeter and the target RNA and so, the polynucleotide sequence is detached from the gold nanoparticles and hybridizes to the target complementary sequence. FAM emission becomes detectable and indicates positive HCV sample.

The term "kit" refers to a composition of matter containing one or more ingredients necessary to practice the method of detecting HCV according to the invention. Preferably, the kit will contain gold nanoparticles and a polynucleotide that binds to hepatitis C virus RNA in separate containers. A kit may also contain at least one biological sample preservative or additive for a sample, such as an agent that prevents degradation of HCV RNA, an RNA extractant buffer for extracting, isolating or purifying HCV RNA from a sample, a reaction buffer in which gold nanoparticles, the polynucleotide binding to HCV RNA and the biological sample are mixed, a negative control sample, a positive control sample, one or more reaction containers, such as tubes or wells, a colorimetric chart, a packaging material, an instruction for use in detecting hepatitis C virus.

The term "subject" includes humans and other primates (e.g., chimpanzee) and other animal models that are susceptible to HCV infection.

The HCV detection method of the invention comprises contacting a sample suspected of containing hepatitis C virus RNA with an oligotargeter polynucleotide (or modified oligotargeter) that binds to hepatitis C virus RNA. Usually the HCV RNA will be extracted or purified from a sample and denatured prior to mixing it with an oligotargeter and the concentration of oligotargeter and salt are carefully selected to permit hybridization as well as subsequent discrimination of samples containing hybridized HCV RNA and oligotargeter from samples not containing HCV RNA after admixture with gold nanoparticles. As noted above, other ingredients for HCV assay ingredients comprise the oligotargeter, a suitable buffer such as a salt-containing hybridization buffer, the sample (RNA), and the gold nanoparticles.

HCV RNA may be extracted from a clinical specimen using a commercial RNA extraction kit, such as those available from Promega. To eliminate hybridization to cell-free DNA or other contaminating DNA, a sample may be treated with DNAse prior to hybridization to an oligotargeter. Denaturation and annealing of a sample may be performed by methods known in the art, such as by use of a thermal cycler, heat block, or water bath. For example, the sample may be denatured at 95° C. and annealed at 60° C. for 1 minute for both steps in PBS buffer at pH 7.0-7.4.

The extracted or purified sample can be diluted with a sample buffer such as PBS or Tris prior to contacting it with a suitable oligotargeter sequence, such as a oligotargeter recognizing all genotypes of HCV or, alternatively, an oligotargeter specific for a particular HCV genotype. It is not necessary to amplify the HCV RNA for this assay. HCV RNA in a sample and the oligotargeter are hybridized under conditions that do not affect the stability of gold colloid or that interfere with sample hybridization to the oligotargeter.

The extracted or purified sample can be diluted with a sample buffer such as PBS or Tris prior to contacting it with a suitable oligotargeter sequence, such as a oligotargeter recognizing all genotypes of HCV or, alternatively, an oligotargeter specific for a particular HCV genotype. It is not necessary to amplify the HCV RNA for this assay.

HCV RNA in a sample and the oligotargeter can be hybridized before the addition of gold nanoparticles as described herein under conditions that do not interfere with sample hybridization to the oligotargeter or subsequently affect the stability of gold colloid used in the colorimetric detection step. Depending on the type of test sample an appropriate ratio of sample to oligotargeter sequences is selected, usually a sample will be contacted with about 500-1,000 nM of oligotargeter and permitted to hybridize for a suitable time, for example, for 1-3 min, at a temperature ranging from 45 to 60 degrees or at room temperature.

While the ratio of oligotargeter to gold nanoparticle content may vary depending on the size of the gold nanoparticles, each gold nanoparticle may be stabilized from salt-induced aggregation when it is covered by about 12 oligotargeter molecules. One example of a suitable ratio of target, oligotargeter and gold nanoparticles would be 7 microliters of extracted RNA of unknown or variable concentration in combination with 1 μM oligotargeter which is admixed with 10 nM gold nanoparticles.

The concentration of gold nanoparticles is also selected to provide a sensitive discrimination of samples containing duplex HCV RNA and oligotargeters from those not containing HCV RNA. As a rough estimate, about 7 molecules of oligotargeter can stabilize a gold nanoparticle and prevent its aggregation. The presence of HCV RNA in a sample will be detected by a colorimetric change which can be visually determined or determined using an instrument.

The sample once contacted with the oligotargeter, denatured, and annealed is mixed with a colloidal gold containing gold nanoparticles and a colorimetric determination is performed where a red-to-blue shift in solution color indicates the presence of HCV RNA complementary to the oligotargeter. When the color of the mixture remains red it indicates the absence of HCV RNA complementary to the oligotargeter. Thus, HCV is detected colorimetrically by a change in color from red to blue where gold nanoparticles aggregate in presence of the HCV RNA:oligotargeter duplexes in comparison with a negative control or a sample not containing the virus where nanoparticles do not aggregate and no color change is observed.

Alternatively, the presence of HCV RNA hybridized to an oligotargeter can be performed using a modified oligotargeter that has been tagged with a fluorescent dye, such as with FAM dye at its 5' terminal, and whose fluorescent emission is quenched when bound to a gold nanoparticle. In this case, the presence of HCV RNA complementary to the oligotargeter will result in a fluorescent signal while samples lacking HCV RNA complementary to the oligotargeter will have their fluorescent emissions quenched by binding to the gold nanoparticles.

The HCV detection method described herein may be used to detect various types of HCV infection, including acute infection, persistent infection or occult HCV infections. It may also be used to follow or monitor HCV infection in a subject either before, during or after treatment for HCV or other diseases or conditions.

Detection of Acute HCV infection: Diagnosis of acute HCV remains a challenge because most infected patients are asymptomatic and antibody tests are unable to recognize acute infection or differentiate between acute and chronic infections. Also, there are no available tests to differentiate between early and late acute HCV infection. Viral RNA is usually detected in the patient's serum within 7-21 days after infection. This makes HCV RNA detection assays in acute infection should be accurate with very low limit of detection. Accurate diagnosis of acute HCV infection is important because early antiviral therapy can lead to better sustained virological response as more than 70% of patients with acute infection respond to therapy while therapeutic response of patients with chronic infected is low and may develop liver cirrhosis which may be further developed to hepatocellular carcinoma. Moreover, therapy of patients with acute infection is more efficacious and the time is shortened compared to therapy in the chronic phase. Also, several issues have been resolved in RNA detection during the acute phase infection as optimal time after infection to initiate therapy (8-12 weeks), optimal treatment duration (24 weeks) and ribavirin is not required for optimal responses during acute infection, thus reducing the risk of major adverse effects. For all the above mentioned reasons, the early detection of HCV RNA during the acute phase plays a critical role in shaping clinical management of acute HCV infection.

Detection of Occult HCV infection: Occult infection is defined as the existence of HCV RNA at levels that are repeatedly undetectable in serum or plasma by current clinical laboratory assays, but are identifiable in serum, peripheral blood mononuclear cells (PBMCs) and/or liver tissue by molecular tests of enhanced sensitivity. Consequently, the proposed assay which has very low detection limit can be used in diagnosis of occult HCV infection. HCV Detection to determine end of treatment and sustained virological response patients: Sustained Virological Response (SVR) is defined as undetectable HCV RNA after 24 weeks of therapy cessation and is an important indicator of the success of HCV treatment. The assay used in detecting HCV RNA at this stage should be highly sensitive because if the SVR result is false negative (i.e. the HCV RNA is present in the serum and the cells, but the detection method or the assay used has high limit of detection that is incapable of detecting these very low viral load), a viral relapse will occur and more resistant viral strains are likely to prevail. Other time points during HCV infection and/or treatment may also be assessed using the method of the invention, for example, monitoring HCV infection at 1, 2, 4, 8, 10, 12, 15, 18, 20, 22 or 24 weeks after cessation of therapy or after a change in drug regimen.

The AuNP-based assay developed by the inventors can be used at this stage to monitor the treatment response and to assure the complete clearance of HCV RNA after cessation of treatment because of its high sensitivity and low detection limit (e.g., 20 viral copies or lower per reaction). However, the sensitivity of the assay may be adjusted depending on the particular clinical or technical application and may detect 200, 150, 100, 75, 50, 40, 30, 20 or fewer viral copies per reaction.

The Examples below are provided only for illustrative purposes and not to limit the scope of the present invention. Numerous embodiments within the scope of the claims will be apparent to those of ordinary skill in the art, thus the following non-limiting examples only describe particular embodiments of the invention.

EXAMPLE 1

Synthesis of AuNPs

A colloidal solution of AuNPs with a diameter of 15 nm±2 was prepared by citrate reduction of hydrogen tetracloroaurate (III) ($HAuCl_4.3H_2O$) as described elsewhere [16]. Briefly, the reflux system was cleaned by aqua regia and then rinsed with ultrapure water, and blown out with $N_2$. An aqueous solution of $HAuCl_4.3H_2O$ (1 mM, 100 mL) was brought to reflux while stirring, then 10 mL of 1 trisodium citrate (38.8 mM) were added quickly. This resulted in consequent change in solution color from yellow to clear to black to purple to deep red. Afterwards, the solution was refluxed for an additional 15 minutes and then allowed to cool to room temperature. The colloidal solution was then filtered through 0.45 µm acetate filter, and transferred into a clean storage glass bottle.

EXAMPLE 2

Characterization of AuNPs

Size and distribution of the prepared AuNPs were characterized using field emission scanning electron microscopy (Model: Leo Supra 55). One drop of the AuNPs solution was added onto a silicon slide that was allowed to air dry before examination. The $\lambda_{max}$ for AuNPs was measured using UV spectrophotometer (Jenway 6800). The concentration of the prepared AuNPs was calculated as described previously [17], which is incorporated by reference.

EXAMPLE 3

Serum Sample Collection and Processing

Seventy five serum samples were collected from healthy volunteers (n=45) and chronic HCV patients (n=30). All samples were negative for hepatitis B surface antigen and hepatitis B antibody. All positive samples have elevated ALT and AST levels. Rapid HCV test was performed on all the samples. Viral load of HCV positive samples was determined by real-time PCR (Artus kit; Qiagen).

HCV RNA Extraction: Extraction of RNA from serum samples was assessed using three different kits: QIAamp Viral RNA kit (Qiagen; Cat. No. 52904), Absolute RNA Miniprep Kit (Stratagene; Cat. No. 400800) according to standard manufacturer's instructions, and SV total RNA isolation system (Promega; Cat. No. Z3100) according to the modified manufacturer's protocol for HCV RNA isolation [18] which is incorporated by reference.

Cell free DNA may fragment and may interfere with the assay. These fragments can lead to false negative results due to their adsorption onto the AuNPs. Therefore, the samples were treated with DNase to exclude cell-free DNA and/or genomic DNA in the sample. Qiagen viral RNA extraction kit, as stated in the kit's instruction manual, does not guarantee the absence of DNA in the final eluted RNA. The Stratagene total RNA kit and Promega RNA extraction kit both include a DNase treatment step.

EXAMPLE 4

RT-PCR and Real Time RT-PCR

Amplification of RNA was done by using Qiagen one step RT-PCR enzyme mix (Cat. Number 210210) using primers targeting the 5'UTR region, forward primer 5'GTGAGGAACTACTGTCTTCACG'3 (SEQ ID NO: 1), and the reverse primer 5'ACTCGCAGGCACCCTATCAGG'3 (SEQ ID NO: 2). The thermal cycling protocol was 50° C. for 30 min (reverse transcriptase reaction), 95° C. for 15 min (Taq activation), and 40 cycles of 1 min at 95° C., 1 min at 55° C., and 1 min at 72° C.; 10 min at 72° C., and then held at 4° C. yielding a product of 265 bp. Real-time RT-PCR was done by AgPath ID One Step RT-PCR kit (cat #AM 1005; Ambion) where 8 µL of the sample were taken and completed to 10 µL with ultra pure water. Amplification was done using a Stratagene Mx3005P.

EXAMPLE 5

Colorimetric AuNPs Assay for Detecting Full Length HCV RNA in Clinical Specimens One oligotargeter that targets 5'UTR of HCV RNA was added to 10 mM phosphate buffer saline solution (PBS, pH=7.0; hybridization buffer). Different concentrations of NaCl in PBS buffer and oligotargeter concentrations were tested to determine appropriate concentrations for performing the assay. Hybridization buffer was prepared using 0.53 M NaCl and 6.66 µM (6.6 pmol/µL) oligotargeter. Different volumes of the AuNPs were tested, and 10 µL of the prepared AuNPs (10 nM) was selected for use in the final assay. As for the oligotargeter used in the assay, two oligotargeter sequences were tested, both targeting the HCV RNA 5'UTR. The first oligotargeter was 22 nucleotides long and the second one was 27 nucleotides long. The second oligotargeter was finally used in this study due to its high specificity to all HCV genotypes and subtypes. In addition, it is not complementary to any human mRNAs as verified by blasting the oligotargeter using NCBI database.

The assay was performed as follows, 7 µL of the extracted RNA were placed in a sterile PCR tube and 3 µL of the hybridization buffer were added and mixed well (final concentration of the oligotargeter and NaCl after addition of AuNPs was 1 µM and 0.08 M, respectively). The mixture was then denatured at 95° C. for 30 seconds, and annealed at 59° C. for 30 seconds and then cooled to room temperature for 10 minutes. 10 µL of colloidal AuNPs were then added to the mixture, and the color was observed within one minute. For a permanent record of the results, one µL of the final mixture was spotted onto a silica plate.

Detection Limit Measurements: HCV positive samples with known viral load, as determined by real-time PCR, were used to determine the detection limit of the colorimetric assay. Serial dilutions of the sample (10-2,000 HCV RNA copies) were tested using the developed method to determine the detection limit of the assay.

Figure 2:
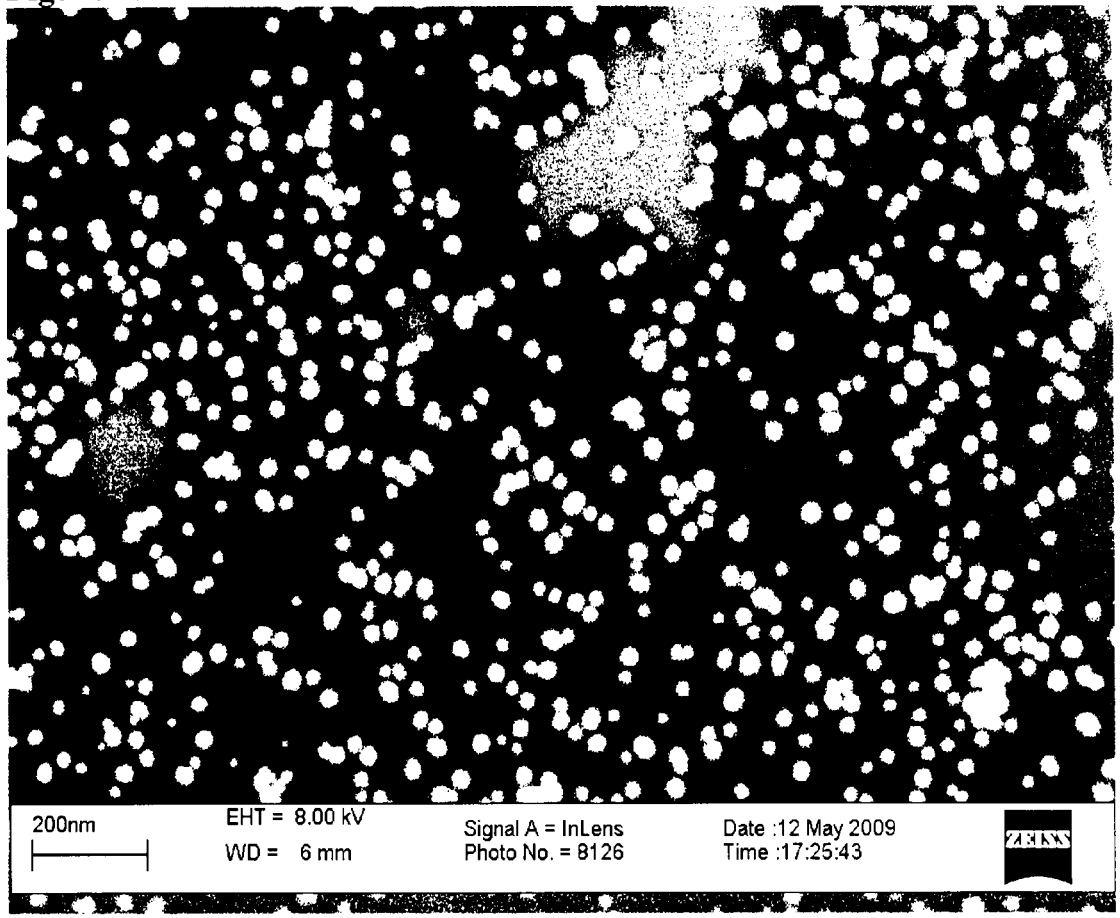
FIG. 2. Scanning electron monographs of the prepared AuNPs. One drop of AuNPs was placed on silicon slide and left to dry then examined using field emission scanning electron microscopy (Model: Leo Supra 55).
Figure 3:
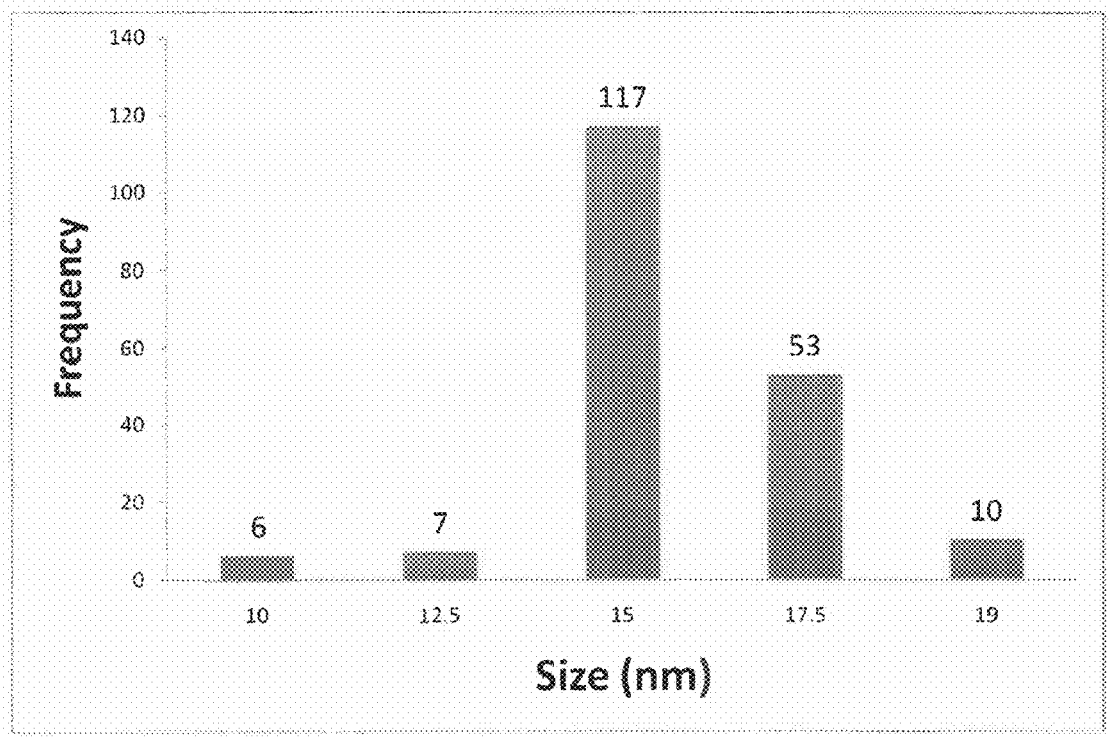
FIG. 3. Analysis of AuNPs size distribution. The scanning electron microscope image in FIG. 2 was analyzed by Image J 1.4 software Wayne Rasband, National Institutes of Health, USA; http://_rsb.info.nih.gov/ij/java 1.6.0_05.

Size Distribution and Surface Plasmon Band of the Prepared AuNPs: Scanning electron microscope image of AuNPs (FIG. 2) was analyzed using the Image 1.41 J software package (Wayne Rasband, National Institutes of health, USA. Http//: rsb.info.nih.gov/ij/Java1.6.0_05). The AuNPs were well dispersed as shown in FIG. 2 and the mean diameter was found to be 15 nm (FIG. 3). The absorption spectrum of the prepared AuNPs displayed a single peak in the visible region with $\lambda_{max}$ at 518-520 nm.

Suitability of RNA Extraction Method: Serum samples may contain some lymphocytes, which contain human mRNA or genomic DNA. Moreover, serum also contains cell-free DNA, and nucleoproteins [19]. Cell free DNA may fragment and adsorb on AuNPs leading to false negative results. Samples were treated with DNase to exclude cell-free DNA and/or genomic DNA. Extracting HCV RNA using Qiagen viral RNA extraction kit has lead to false negative results even in samples containing very high viral titers. On the other hand, reproducible results were obtained using RNA extraction kits that employ DNase treatment (Stratagene total RNA kit and Promega RNA extraction kit).

Colorimetric AuNPs Assay: Development: The color of AuNPs colloidal solution is affected by four main factors which the inventors have found should be adequately selected and controlled for best results. These are concentrations of NaCl, AuNPs, and oligotargeter used, and the assay temperature.

AuNPs were prepared using the citrate reduction method which produces negatively charged nanoparticles due to citrate coating on their surfaces. This negative charge prevents their aggregation and a red color is maintained. Salt induces gold nanoparticle aggregation leading to a red-to-blue shift in solution color. A final concentration of 0.08 M NaCl was determined to be sufficient for aggregation of AuNPs and visual detection of the color change, and at the same time, sufficient for proper annealing of the oligotargeter to its target.

Although ssDNA oligotargeters adsorb on AuNPs and prevent their aggregation, the inventors found that concentration of the oligotargeters should be carefully selected and controlled. This is because, in the absence of the target, a very low oligotargeter concentration will not be sufficient to prevent aggregation leading to a false positive result. On the other hand, in the presence of the target, a very high oligotargeter concentration will prevent aggregation leading to a false negative result. In this study, at a final salt concentration of 0.08 M, a oligotargeter concentration less than 0.2 µM was unable to prevent aggregation of 10 nM 15 nm AuNPs in the absence of the target. On the other hand, a final oligotargeter concentration more than 3 µM was too high for any aggregation to occur in the presence of the target. Consequently, the inventors found that an appropriate oligotargeter concentration was about 1 µM in the total assay volume. The concentrations of the gold nanoparticles and salt are dependent on the oligotargeter concentration. In general, the oligotargeter concentration ranges from 0.5 to 3 uM at 50 to 300 mM salt and 7 to 17 nM gold nanoparticle concentration.

The concentration of 15-nm AuNPs used in the assay was 10 nM in a total assay volume of 20 µL. This concentration is sufficient for visual detection of the color change, together with the oligotargeter and salt concentrations discussed above. Change in solution color was not clear and false results were obtained when lower concentrations of AuNPs were used.

Performing the assay without heating (necessary for RNA denaturation and annealing of oligotargeters) may lead to irreproducible results for most of the samples (false positives and/or negatives). Consequently, denaturation and annealing steps were performed before the addition of the AuNPs to increase the specificity of the assay. It should be noted that the addition of AuNPs directly after removal of the tubes from the thermal cycler (while the tubes are still hot), resulted in false positive results. Therefore, the mixture must stand at room temperature for 10 to 15 minutes prior to addition of AuNPs in order to obtain reproducible results. Increasing the time of the denaturation and annealing steps also increases the percentage of false positive results. In our opinion, increasing the time of denaturation and annealing might increase the probability of the oligotargeter annealing non-specifically to some escaped nucleic acids other than HCV RNA that may be found in the nucleoprotein complexes in the serum.

Figure 4:
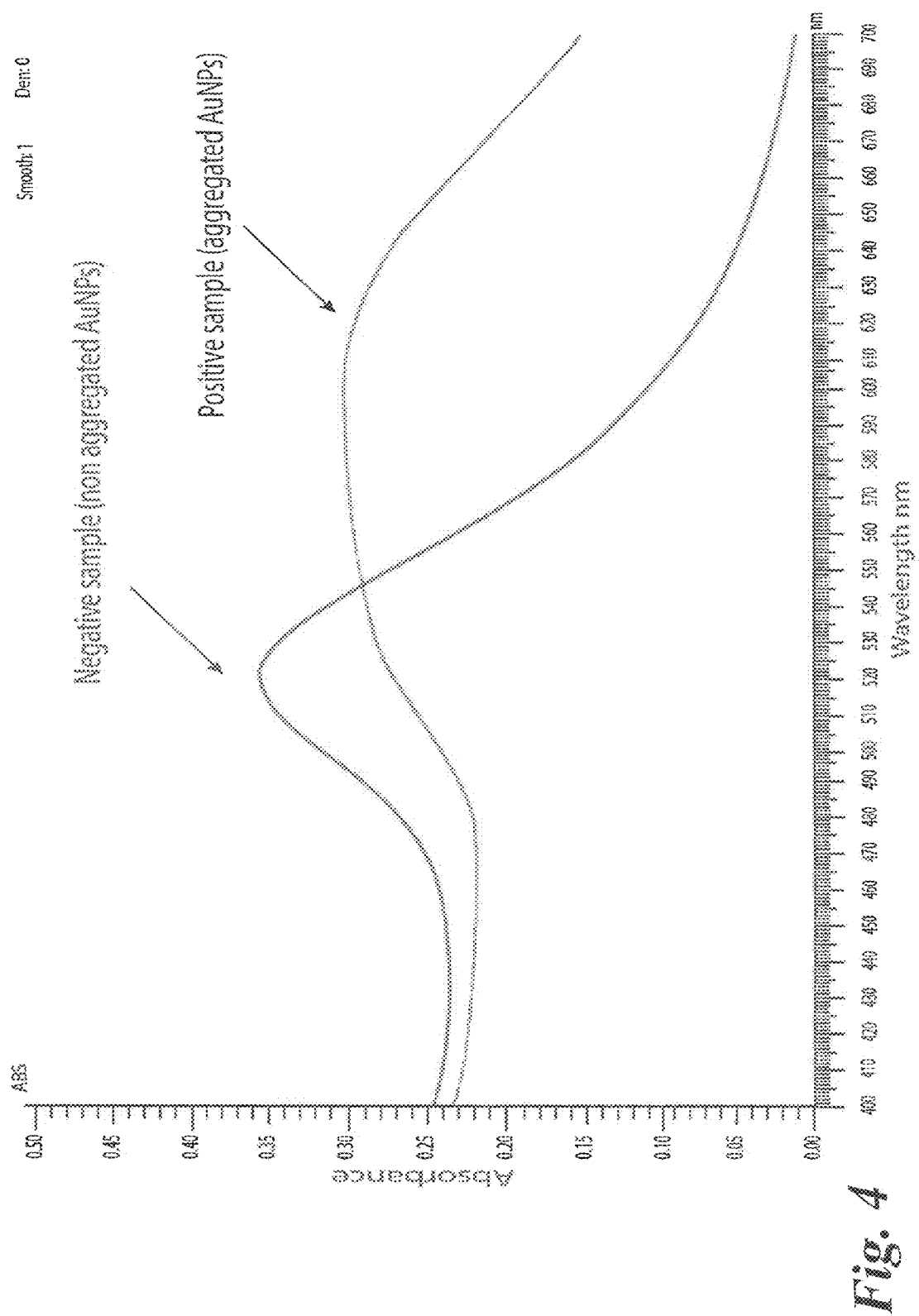
FIG. 4. Extinction spectra of positive and negative samples. The absorption spectra of positive sample (aggregated AuNPs, black) and negative sample (non-aggregated AuNPs, red). Note the red shift and broadening of the peak of the positive sample due to aggregation of AuNPs. For the negative sample, the $\lambda_{max}$ was around 518-520 nm.
Figure 5A:
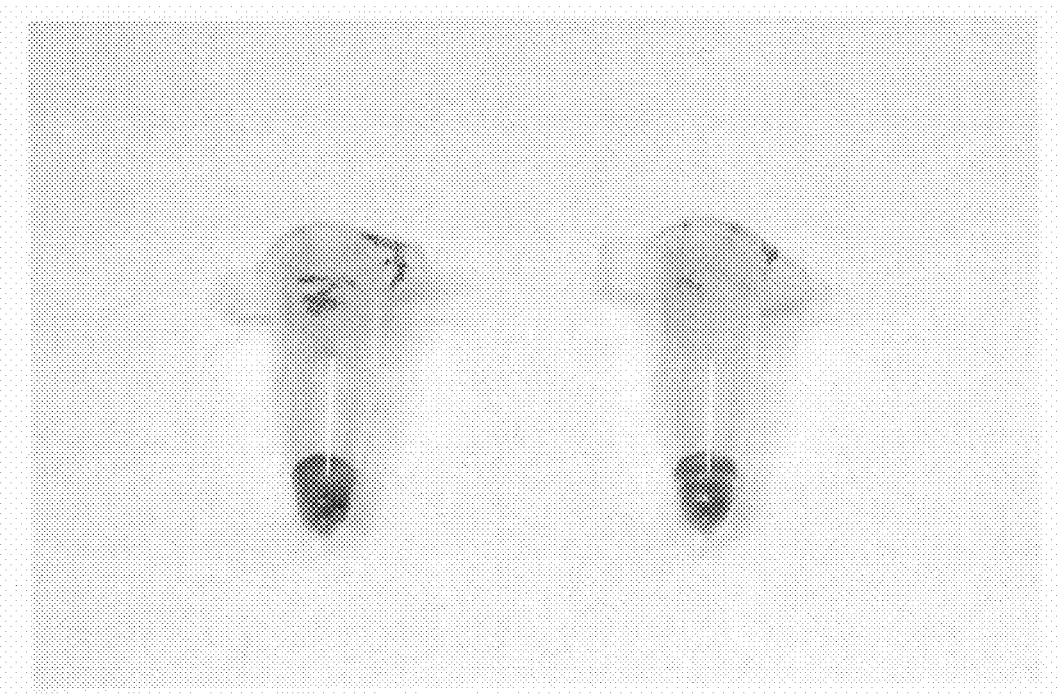
FIG. 5. Colorimetric HCV RNA assay using unmodified AuNPs. Each tube contains 7 μL sample, 1 μM oligotargeter and 0.08 M NaCl. The samples were denatured at 95° C. for 30 seconds and annealed at 60° C. for 30 seconds and then 10 μA of 15 nm AuNPs was added after cooling the mixture at room temperature for 10 minutes. The photographs were taken after 1 minute from the addition of the AuNPs. (a) HCV RNA negative samples and (b) HCV RNA positive samples. Note the change in color from red to blue in the positive samples.
Figure 5B:
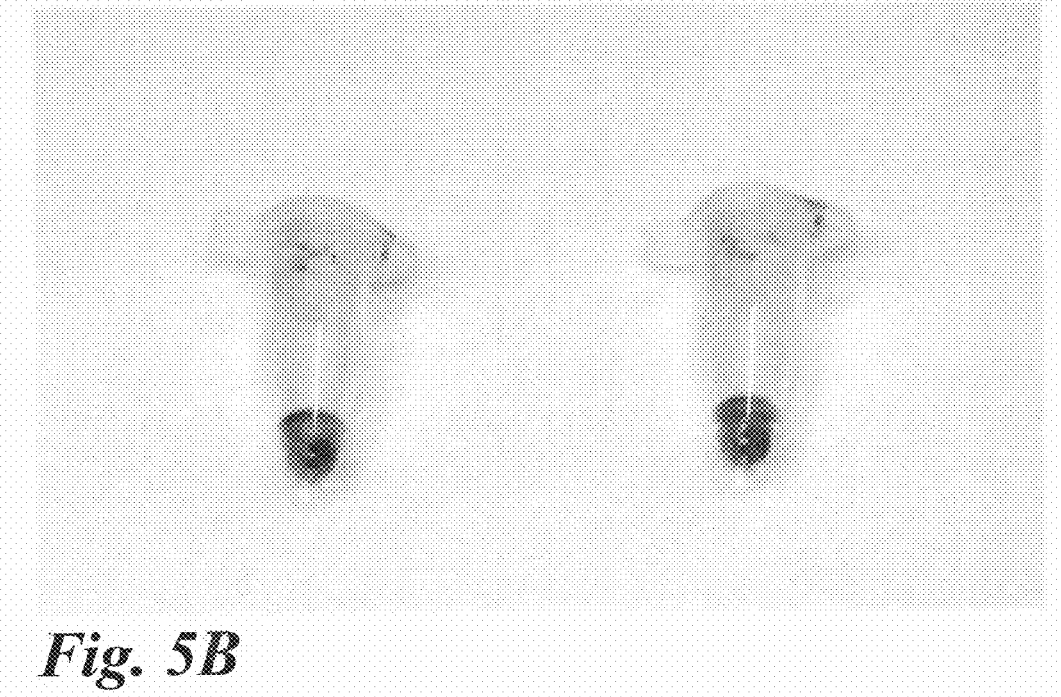
Figure 6:
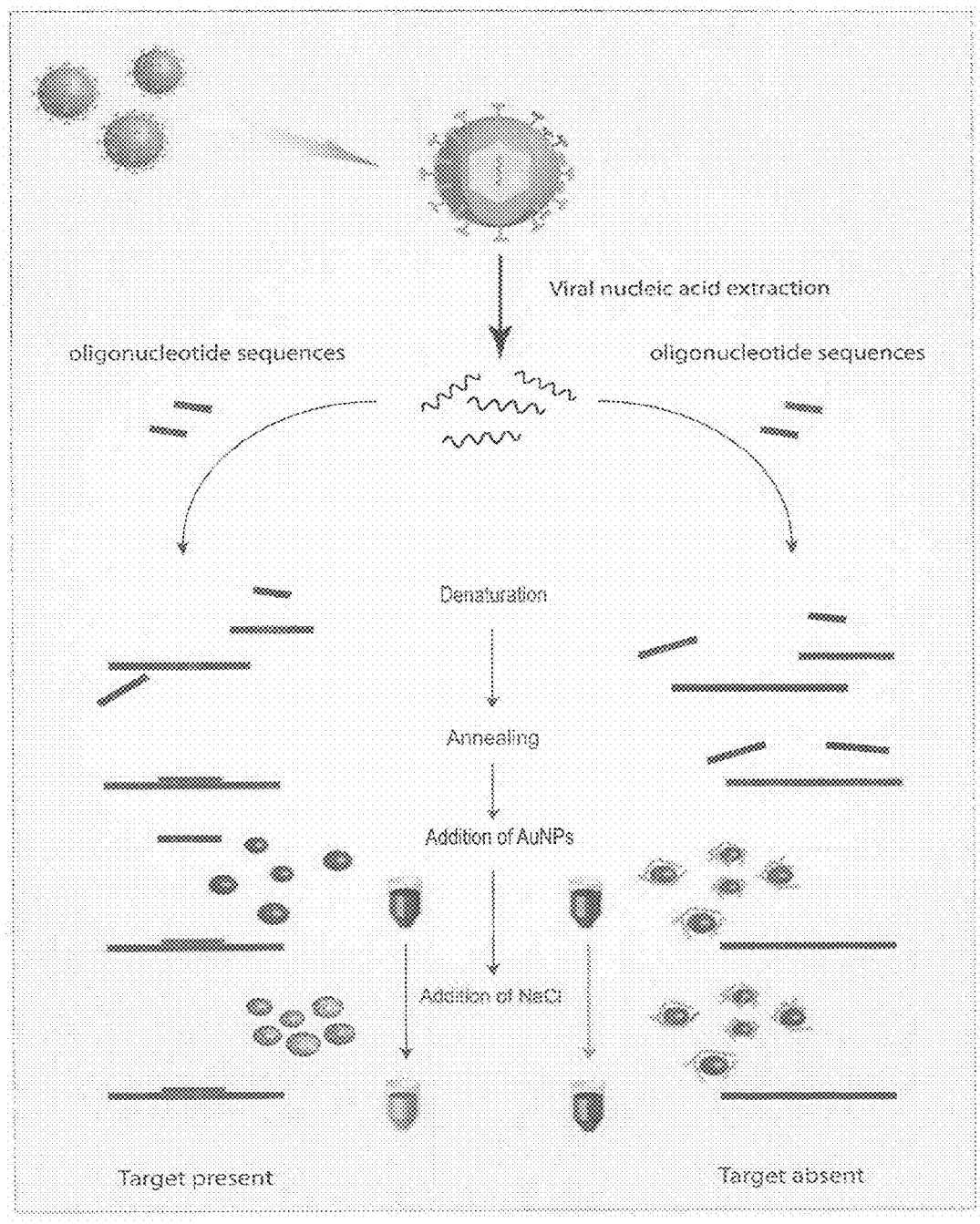
FIG. 6 Detailed schematic diagram of a colorimetric assay based on unmodified AuNPs for detection of full length HCV RNA.

In summary, after adding the hybridization buffer to the extracted RNA, the mixture was subjected to denaturation at 95° C. for 30 seconds, annealing at 59° C. for 30 seconds, and then cooling to room temperature before the addition of the AuNPs. The change in color was visualized within only one minute. Also, change in the AuNPs absorption spectra was measured (FIG. 4). 28 out of 30 HCV positive samples gave a blue color and 40 out of 45 HCV negative samples gave a red color (FIG. 5). Based on these results, the assay has a sensitivity of 92% and a specificity of 88.9%.

Real-time RT-PCR was used to calculate the HCV viral load in clinical specimens that ranged from 43 IU/mL to 12,000 IU/mL. Serial dilutions of the HCV RNA (25-2000 HCV RNA copies) were prepared and assayed using the AuNPs as described above. The assay was capable of detecting 20 HCV copies/reaction.

EXAMPLE 6

Comparison to Conventional HCV Assays

The assay developed by the inventors was compared to commercial realtime RT-PCR method and in-house conventional RT-PCR method. Fifteen HCV positive samples and five negative samples were tested by realtime RT-PCR and the AuNP-based method. There was a 100% concordance (15/15) between the developed assay and Taqman realtime PCR (Ambion) results for HCV positive samples. However, 4/5 samples were negative by both assays and one negative sample tested positive by the new assay. On the other hand, two samples that were borderline positive by conventional RT-PCR tested positive by the developed assay and the results were further confirmed by realtime RT-PCR. These results show that the new assay has comparable performance to conventional and realtime RT-PCR.

Incorporation by Reference

Each document, patent, patent application or patent publication cited by or referred to in this disclosure is incorporated by reference in its entirety, especially with respect to the specific subject matter surrounding the citation of the reference in the text. However, no admission is made that any such reference constitutes background art and the right to challenge the accuracy and pertinence of the cited documents is reserved.

REFERENCES

[1] WHO.
[2] M. Higuchi, E. Tanaka, and K. Kiyosawa, Epidemiology and clinical aspects on hepatitis C. Jpn J Infect Dis 55 (2002) 69-77.
[3] G. M. Lauer, and B. D. Walker, Hepatitis C virus infection. N Engl J Med 345 (2001) 41-52.
[4] D. B. Strader, T. Wright, D. L. Thomas, and L. B. Seeff, Diagnosis, management, and treatment of hepatitis C. Hepatology 39 (2004) 1147-71.
[5] P. Marcellin., Hepatitis C: clinical spectrum of the disease. J Hepatol. 31 (1999) 9-16.
[6] Sarrazin, Diagnosis of hepatitis C: update. J Gastroenterol Hepatol J Gastroenterol Hepatol (2004) S88-S93.
[7] J. D. Scott, and D. R. Gretch, Molecular Diagnostics of Hepatitis C Virus Infection: A Systematic Review. JAMA 297 (2007) 724-732.
[8] K. K. Jain, Nanotechnology in clinical laboratory diagnostics. Clin Chim Acta 358 (2005) 37-54.
[9] P. K. Jain, K. S. Lee, I. H. El-Sayed, and M. A. El-Sayed, Calculated Absorption and Scattering Properties of Gold Nanoparticles of Different Size, Shape, and Composition: Applications in Biological Imaging and Biomedicine. J. Phys. Chem. B 110 (2006) 7238-7248.
[10] L.H.a.R. L J, Label-free colorimetric detection of specific sequences in genomic DNA amplified by the polymerase chain reaction. J. Am. Chem. Soc. 126 (2004) 4.
[11] J. P. Huang X, El-Sayed I H, El-Sayed M A, Gold nanoparticles: interesting optical properties and recent applications in cancer diagnostics and therapy. Nanomed 2 (2007) 13.

[12] S. H. Radwan, and H. M. Azzazy, Gold nanoparticles for molecular diagnostics. Expert Rev Mol Diagn 9 (2009) 511-24.
[13] H. Li, and L. Rothberg, Colorimetric detection of DNA sequences based on electrostatic interactions with unmodified gold nanoparticles. Proc Natl Acad Sci USA 101 (2004) 14036-9.
[14] J. Griffin, A. K. Singh, D. Senapati, P. Rhodes, K. Mitchell, B. Robinson, E. Yu, and P. C. Ray, Size- and distance-dependent nanoparticle surface-energy transfer (NSET) method for selective sensing of hepatitis C virus RNA. Chemistry 15 (2009) 342-51.
[15] J. Griffin, A. K. Singh, D. Senapati, E. Lee, K. Gaylor, J. Jones-Boone, and P. C. Ray, Sequence-specific HCV RNA quantification using the size-dependent nonlinear optical properties of gold nanoparticles. Small 5 (2009) 839-45.
[16] J. J. Storhoff, R. Elghanian, R. C. Mucic, C. A. Mirkin, and R. L. Letsinger, One-Pot Colorimetric Differentiation of Polynucleotides with Single Base Imperfections Using Gold Nanoparticle Probes. J. Am. Chem. Soc. 120 (1998) 1959-1964.
[17] X. Liu, M. Atwater, J. Wang, and Q. Huo, Extinction coefficient of gold nanoparticles with different sizes and different capping ligands. Colloids Surf B Biointerfaces 58 (2007) 3-7.
[18] D. K. Paul Otto, Rex Bitner, Suzanne Huber and Karl Volkerding, Separate Isolation of Genomic DNA and Total RNA from Single Samples Using the SV Total RNA, promega notes, 1998, pp. 6.
[19] K. L. Sisco, Is RNA in serum bound to nucleoprotein complexes? Clin Chem 47 (2001) 1744-5.
[20] K. Seme, M. Poljak, D. Z. Babic, T. Mocilnik, and A. Vince, The role of core antigen detection in management of hepatitis C: a critical review. J Clin Virol 32 (2005) 92-101.
[21] M. K. El Awady, H. M. Azzazy, A. M. Fahmy, S. M. Shawky, N. G. Badreldin, S. S. Yossef, M. H. Omran, A. R. Zekri, and S. A. Goueli, Positional effect of mutations in 5'UTR of hepatitis C virus 4a on patients' response to therapy. World J Gastroenterol 15 (2009) 1480-6.
[22] Y. Wang, W. Qian, Y. Tan, and S. Ding, A label-free biosensor based on gold nanoshell monolayers for monitoring biomolecular interactions in diluted whole blood. Biosens Bioelectron 23 (2008) 1166-70.
[23] V. B. L A Dykman, Gold nanoparticles: preparation, functionalisation and applications in biochemistry and immunochemistry. Russian chemical Reviews 76 (2007) 14.
[24] M. Green, and P. O'Brien, A simple one phase preparation of organically capped gold nanocrystals. Chemical Communications (2000) 183-184.

The invention claimed is:

1. A method for detecting hepatitis C virus (HCV) comprising:
    contacting unamplified RNA obtained from a patient suspected of being infected with HCV with a single-stranded DNA oligotargeter that ranges in length from 19 to 31 contiguous bases and that binds to HCV RNA, for a time and under conditions sufficient for the unamplified HCV RNA and oligotargeter to hybridize,
    contacting a mixture of the HCV RNA and oligotargeter DNA with non-functionalized gold nanoparticles, and
    detecting HCV RNA in the sample when the gold nanoparticles aggregate,
    wherein aggregated gold nanoparticles exhibit a blue color and non-aggregated gold nanoparticles exhibit a red color.

2. The method of claim 1, wherein the sample is blood or plasma.

3. The method of claim 1, wherein the sample is serum, optionally containing EDTA.

4. The method of claim 1, wherein the sample is saliva.

5. The method of claim 1, wherein the sample is urine.

6. The method of claim 1, wherein the gold nanoparticles are spherical and have an average diameter of 12 to 20 nm.

7. The method of claim 1, wherein the gold nanoparticles are spherical and have an average diameter of 15-18 nm.

8. The method of claim 1, wherein the oligotargeter that binds to HCV RNA comprises a portion of a 5' untranslated region of HCV genomic RNA.

9. The method of claim 1, wherein the oligotargeter that binds to HCV RNA comprises a portion of HCV genomic RNA other than the 5' untranslated region.

10. The method of claim 1, wherein the oligotargeter that binds to HCV RNA contains 20 to 30 contiguous nucleotides.

11. The method of claim 1, wherein the oligotargeter that binds to HCV RNA is a modified oligotargeter containing inosine or having a modified backbone.

12. The method of claim 1, wherein the oligotargeter that binds to HCV RNA is specific to a particular HCV genotype.

13. The method of claim 1, wherein the oligotargeter that binds to HCV RNA binds to all HCV genotypes.

14. The method of claim 1, wherein the sample is obtained from a subject suspected of having acute HCV infection.

15. The method of claim 1, further comprising isolating or purifying RNA in the sample prior to contacting it with the oligotargeter and the gold nanoparticles.

16. The method of claim 1, wherein the aggregation of gold nanoparticles occurs in solution.

17. The method of claim 1, further comprising exposing the sample to conditions which denature HCV RNA.

18. The method of claim 1, wherein the sample is obtained from a subject suspected of having a chronic HCV infection.

19. The method of claim 1, comprising obtaining one or more longitudinal samples from a subject undergoing treatment for HCV treatment.

20. The method of claim 1, comprising obtaining at least one sample from a subject at least 24 weeks after cessation of anti-HCV therapy.

21. The method of claim 1, wherein said subject has, or is suspected of having an acute HCV infection.

22. The method of claim 1, wherein said subject has, or is suspected of having an occult HCV infection.

23. The method of claim 1, comprising contacting said sample with the oligotargeter 5' TACCACAAGGC-CTTTCGCGACCCAACA'3 (SEQ ID NO: 12).

24. The method of claim 1, comprising contacting said sample with at least one oligotargeter selected from the group consisting of SEQ ID NO: 3, 4, 5, 6, 7, 8, 9, 10 and 11.

25. The method of claim 1, wherein the 5' end of the oligotargeter has been conjugated to an FAM dye or other fluorescent dye or fluorophore whose emission can be quenched by gold nanoparticles; and wherein the presence of HCV is detected by the emission of fluorescence.

26. The method in claim 1, further comprising determining an HCV genotype and subtype of HCV in the sample by detecting SNPs in PCR-amplified or unamplified sequences from HCV core, 5'UTR, or NS5B regions.

27. The method according to claim 1, wherein the unmodified AuNPs are citrate-coated AuNPs.

28. The method according to claim 1, wherein the oligo-targeter is not labelled.

* * * * *

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Synthetic Oligonucleotide, forward PCR primer

<400> SEQUENCE: 1
gtgaggaact actgtcttca cg                                              22

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide, reverse PCR primer

<400> SEQUENCE: 2
actcgcaggc accctatcag g                                               21

<210> SEQ ID NO 3
<211> LENGTH: 31
<212> TYPE: DNA
<213> ORGANISM: Artificial Sequence
<220> FEATURE:
<223> OTHER INFORMATION: Synthetic Oligonucleotide, genotype-specific
      oligotargeter

<400> SEQUENCE: 3
cacagataac gactaagtcg tcgccacaca c                                    31

<210> SEQ ID NO 4
<211> LENGTH: 27
<212> TYPE: DNA
<213> ORGANISM: Artificial Sequence
<220> FEATURE:
<223> OTHER INFORMATION: Synthetic Oligonucleotide, genotype-specific
      oligotargeter
```

```
<400> SEQUENCE: 4
gccttgggga taggttgtcg ccttcca                                          27

<210> SEQ ID NO 5
<211> LENGTH: 25
<212> TYPE: DNA
<213> ORGANISM: Artificial Sequence
<220> FEATURE:
<223> OTHER INFORMATION: Synthetic Oligonucleotide, genotype-specific
      oligotargeter

<400> SEQUENCE: 5
tagggcccag gggtatcctg gtttt                                            25

<210> SEQ ID NO 6
<211> LENGTH: 25
<212> TYPE: DNA
<213> ORGANISM: Artificial Sequence
<220> FEATURE:
<223> OTHER INFORMATION: Synthetic Oligonucleotide, genotype-specific
      oligotargeter

<400> SEQUENCE: 6
cagaggccaa ggatatcctg gcttt                                            25

<210> SEQ ID NO 7
<211> LENGTH: 21
<212> TYPE: DNA
<213> ORGANISM: Artificial Sequence
<220> FEATURE:
<223> OTHER INFORMATION: Synthetic Oligonucleotide, genotype-specific
      oligotargeter

<400> SEQUENCE: 7
cgccttgggg ataggctgtc g                                                21

<210> SEQ ID NO 8
<211> LENGTH: 26
<212> TYPE: DNA
<213> ORGANISM: Artificial Sequence
<220> FEATURE:
<223> OTHER INFORMATION: Synthetic Oligonucleotide, genotype-specific
      oligotargeter

<400> SEQUENCE: 8
tcctggttgt gcccaggacc ttccct                                           26

<210> SEQ ID NO 9
<211> LENGTH: 25
<212> TYPE: DNA
<213> ORGANISM: Artificial Sequence
<220> FEATURE:
<223> OTHER INFORMATION: Synthetic Oligonucleotide, genotype-specific
      oligotargeter

<400> SEQUENCE: 9
ttgcgaccgt tccgaattct tccga                                            25

<210> SEQ ID NO 10
<211> LENGTH: 23
<212> TYPE: DNA
<213> ORGANISM: Artificial Sequence
<220> FEATURE:
<223> OTHER INFORMATION: Synthetic Oligonucleotide, genotype-specific
      oligotargeter
```

```
-continued

<400> SEQUENCE: 10
cctttagtac atcctgataa tgt                                                    23

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide, genotype-specific
      oligotargeter

<400> SEQUENCE: 11
cagccctcat tcccataaag                                                        20

<210> SEQ ID NO 12
<211> LENGTH: 27
<212> TYPE: DNA
<213> ORGANISM: Artificial Sequence
<220> FEATURE:
<223> OTHER INFORMATION: Synthetic Oligonucleotide, HCV-specific
      oligotargeter

<400> SEQUENCE: 12
taccacaagg cctttcgcga cccaaca                                                27
```